United States Patent [19]
Johansson et al.

[11] Patent Number: 5,585,551
[45] Date of Patent: Dec. 17, 1996

[54] METHOD FOR IDENTIFICATION OF DIFFERENT STATES OF WATER, AND SENSOR ARRANGEMENT FOR USE IN THE METHOD

[75] Inventors: Reijo Johansson, Kangasala; Paul Wetzer; Juhani Mäkinen, both of Tampere, all of Finland

[73] Assignee: Labko Ice Detection Oy, Kangasala, Finland

[21] Appl. No.: 352,561

[22] Filed: Dec. 9, 1994

[30] Foreign Application Priority Data

Dec. 9, 1993 [FI] Finland ................................ 935594

[51] Int. Cl.$^6$ ........................... B64D 15/20; G01N 29/02
[52] U.S. Cl. ................... 73/64.53; 73/170.26; 340/5.82; 340/962
[58] Field of Search .............................. 73/64.53, 64.42, 73/590, 597, 170.26; 340/582, 962

[56] References Cited

U.S. PATENT DOCUMENTS

| | | | |
|---|---|---|---|
| 4,054,255 | 10/1977 | Magenheim | 244/134 F |
| 4,335,613 | 6/1982 | Luukkala | 73/599 |
| 4,404,852 | 9/1983 | Goto | 340/582 X |
| 4,604,612 | 8/1986 | Watkins et al. | 340/582 |
| 4,628,736 | 12/1986 | Kirby et al. | 73/590 |
| 5,467,944 | 11/1995 | Luukkala | 340/582 |

FOREIGN PATENT DOCUMENTS

| | | |
|---|---|---|
| 90957 | 1/1994 | Finland . |
| 91953 | 5/1994 | Finland . |

*Primary Examiner*—Michael Brock
*Attorney, Agent, or Firm*—Pollock, Vande Sande & Priddy

[57] ABSTRACT

A sensor arrangement for identifying various states of water on a surface of a structure, comprises a sensor element and a transmitter-receiver unit. The sensor element, adapted to be placed on the surface, has two ends and is made of an acoustically conductive material. The transmitter-receiver unit is connected between the two ends of the sensor element. The transmitter-receiver unit alternately transmits acoustic signals to each of the two ends and receives acoustic signals corresponding to the transmitted signals from each of the two ends for subsequent processing.

24 Claims, 7 Drawing Sheets

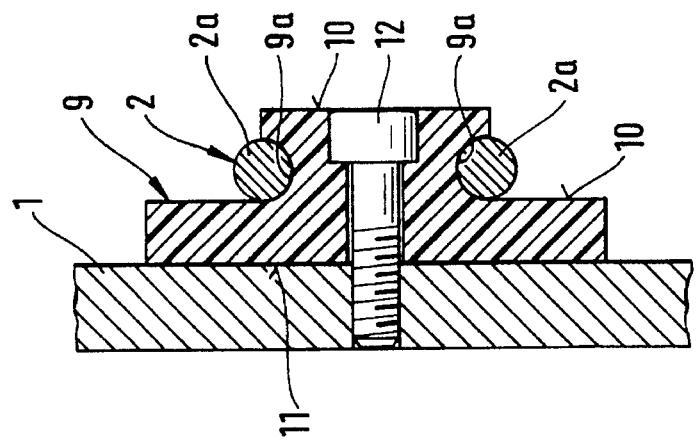
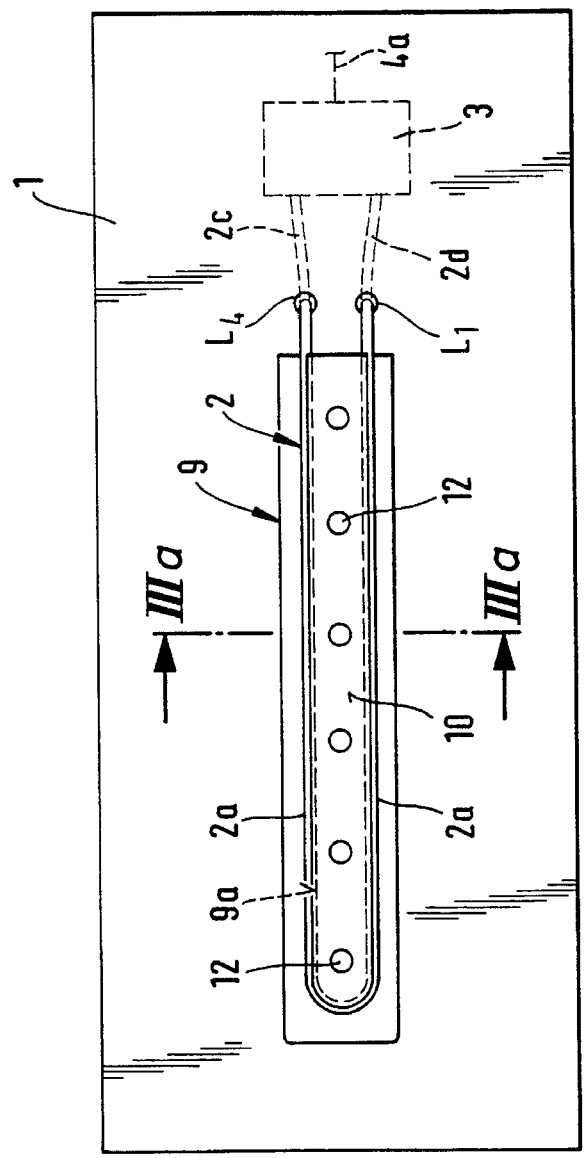

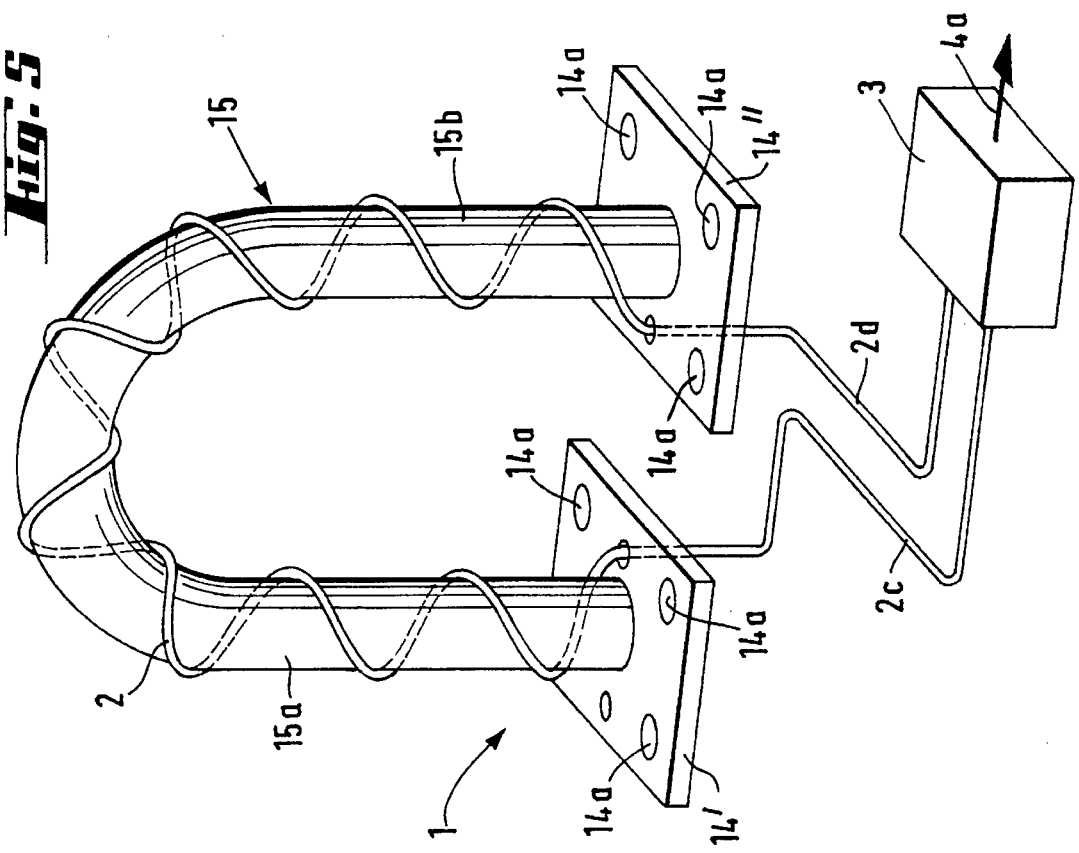
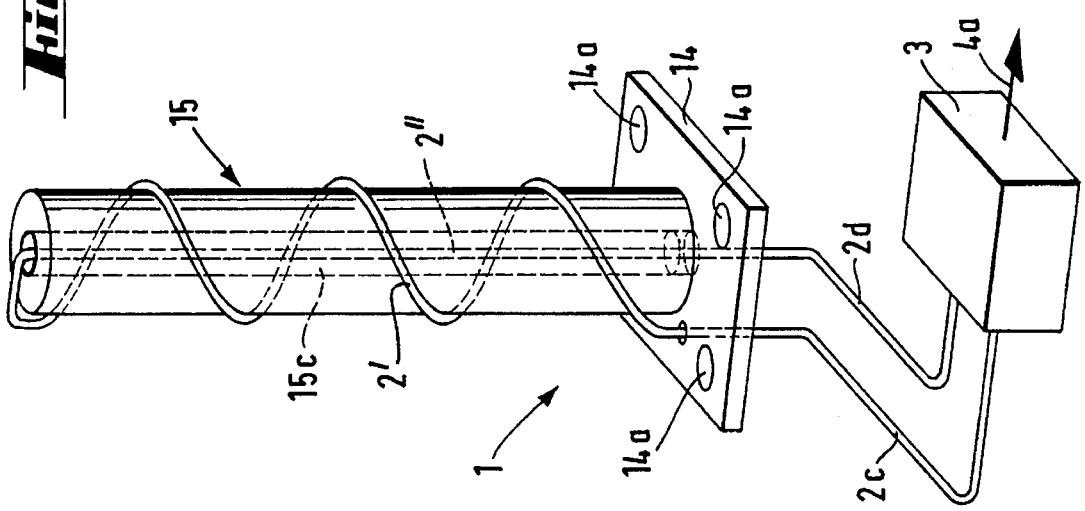

5,585,551

METHOD FOR IDENTIFICATION OF DIFFERENT STATES OF WATER, AND SENSOR ARRANGEMENT FOR USE IN THE METHOD

FIELD OF THE INVENTION

The invention relates to a method for identification of different states of water on the surface of a structure upon which a sensor element has been placed. The sensor element is made of a material conveying acoustic oscillation and is connected at its ends to a transmitter-receiver unit.

The invention also relates to a sensor arrangement for identification of different states of water on the surface of a structure upon which at least the sensor element of the sensor arrangement is placed. The sensor arrangement comprises at least one longitudinal sensor element made of a material conveying acoustic oscillation and a transmitter-receiver unit coupled with the ends of the sensor element, for transmitting acoustic oscillation, preferably oscillation effective in the ultrasonic range, and for receiving the response of the transmitted oscillation.

BACKGROUND OF THE INVENTION

As to the prior art in the field, reference is made to the publication GB-1,117,664. The solution disclosed in this publication cannot, however, be used for reliable identification of the formation of ice on the structure upon which the sensor arrangement is placed, particularly under demanding conditions. In particular, it is impossible to distinguish between the different states of water. Further, it is impossible to locate a change in the state particularly within the range of placement of the sensor arrangement.

SUMMARY OF THE INVENTION

It is an object of the present invention to provide a method for achieving particularly precise identification of the different states of water from a medium, for example the atmosphere or water, in which the sensor arrangement is placed, within the measuring range of the sensor arrangement, detecting a local change in the state, as well as a continuously checking the working order of the sensor arrangement. For achieving these objects, the method of the invention is primarily characterized by transmitting acoustic oscillation to the sensor element by the transmitter-receiver unit alternately from both ends of the same and receiving the response of the acoustic oscillation from both ends of the sensor element.

It is also an object of the present invention to provide a sensor arrangement which is primarily characterized in that the transmitter-receiver unit is arranged to transmit oscillation and to receive the response of the transmitted oscillation from both ends of the sensor element.

The measurement carried out by the method and by the sensor arrangement is based on measuring the attenuation of the oscillation generated in the sensor element, the oscillation penetrating different states of water in the measuring range of the sensor element. The frequency of the oscillation to be generated is preferably an ultrasound outside the hearing range of the human ear. The oscillation is transmitted by the transmitter-receiver unit preferably in pulse form or pulse burst form. The amplitude of this oscillation is reduced, if the water in the measuring range of the sensor arrangement begins to freeze via slush formation. The response of the transmitted oscillation received as the measuring result can be scaled such in a way that the result obtained for water in the measuring range has a numerical value of about 1.0, for slush about 0.6 and for ice about 0.2 to 0.0. In accordance with the present invention, when oscillation is transmitted to the sensor element in both directions and received from both directions, it is possible to verify a local change of state exactly in the measuring range of the sensor arrangement. Thus the front edge of the local change of state (the edge receiving the oscillation transmitted from the transmitter-receiver unit in the transmitting direction) indicates a first response (return reverberation) in the direction opposite to the transmitted oscillation along the sensor element reflected back to the transmitter-receiver unit. The time taken in this operation can be measured and multiplied by the travelling speed of the pulse, for example 5000 m/s, to obtain the distance to-and-fro. The sensor element is fixed in the structure either directly or by means of a support according to one embodiment of the invention, whereby the oscillation at the change of state is transferred to the structure whose surface is monitored. Thus, the second response of the oscillation can be received at the end of the sensor element opposite the transmitting end. Consequently, the time spent between sending oscillation and receiving either one or both of the responses is shorter than the time required for penetrating the sensor element in a normal situation. These measurements can be made at both ends of the sensor element at certain intervals as automatic pulses or pulse bursts in opposite directions. By the method presented above, the beginning of the change of state of water is determined in a reliable way, and the location is thus defined on the basis of the time interval between sending the oscillation and receiving the response. The frequency of the oscillation exceeds 20 kHz up to 300 kHz. It is important to choose the frequency so that it exceeds the frequencies of free vibration in the structure 1.

Particularly in a case when the sensor element of the sensor arrangement is damaged and broken, the oscillation will not penetrate the sensor element. Thus, the only available response is the response of the transmitted oscillation returned from the cut-off point to the transmitting end of the sensor element, which has substantially retained its amplitude. By the method and sensor arrangement of the invention, it is possible to locate the cut-off point and also to check the sensor element by measuring the time difference between the oscillation leaving and returning from both ends of the sensor element with a known travelling speed of the oscillation.

BRIEF DESCRIPTION OF THE DRAWINGS

The invention will be illustrated in more detail by the following description with reference to the appended drawings. In the drawings, FIG. 3 is a schematic view of a second embodiment of the sensor arrangement, where the sensor element is pre-installed on a support with the shape of a longitudinal form part fixed in a structure, different states of water being identified on the surface of the same, whereby partial FIG.

Figure 6:
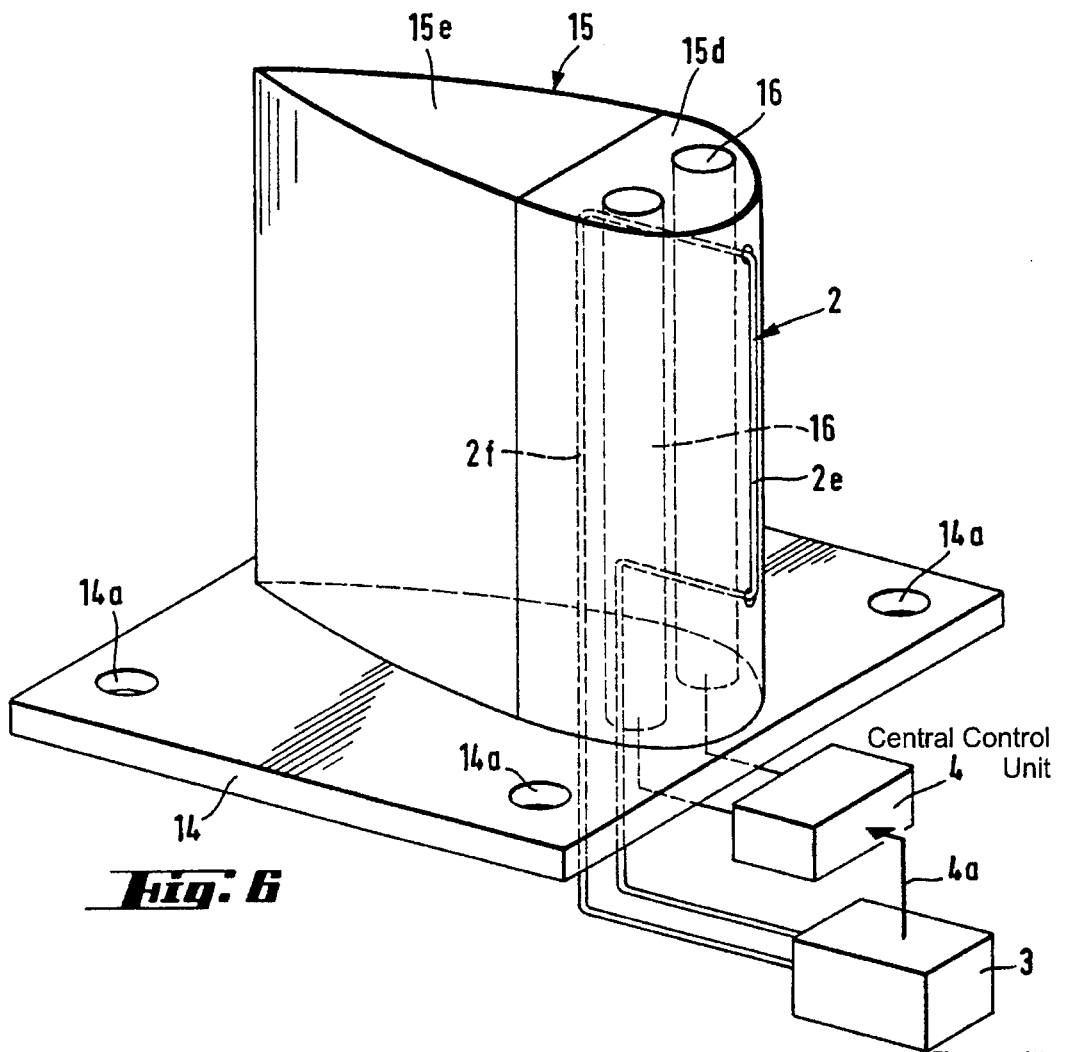
Figure 7:
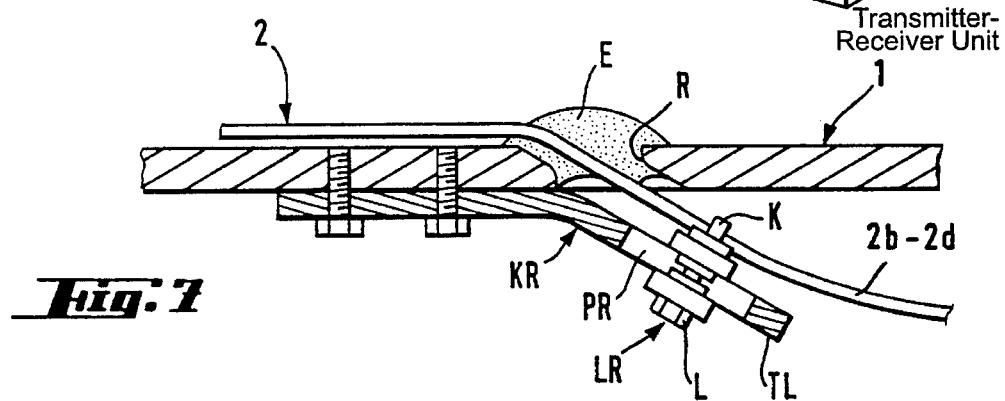
Figure 8:
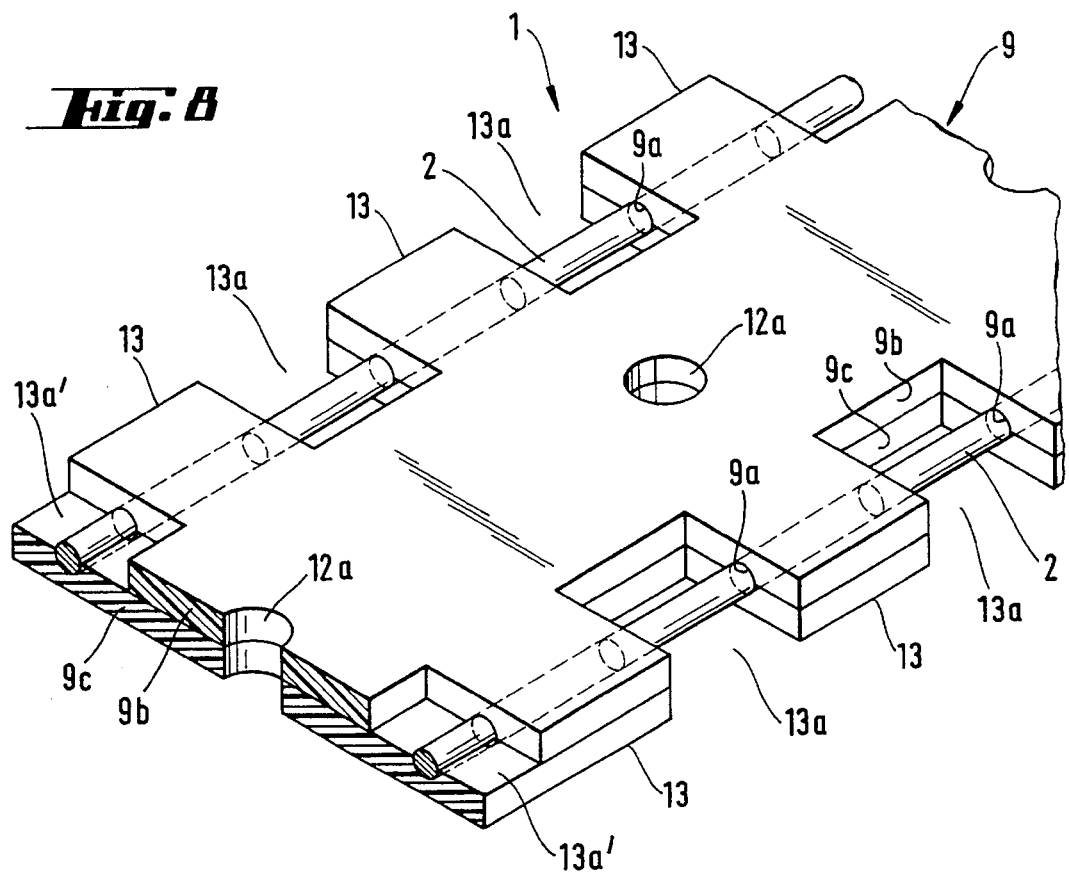
Figure 9:
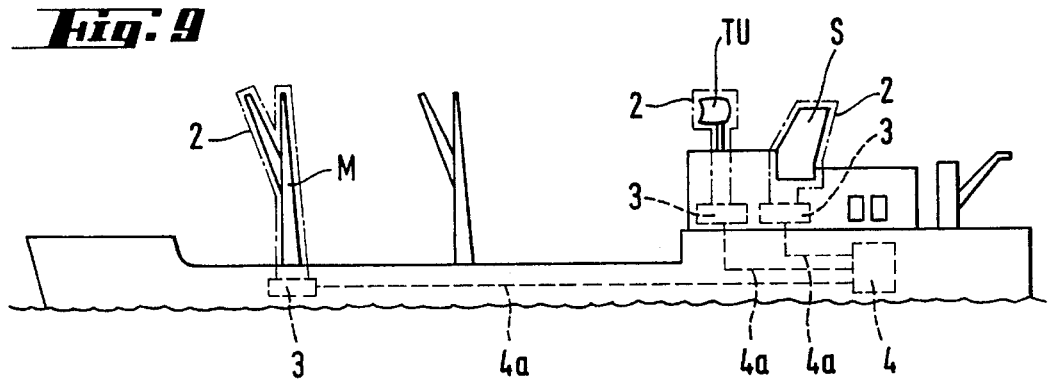
Figure 10:
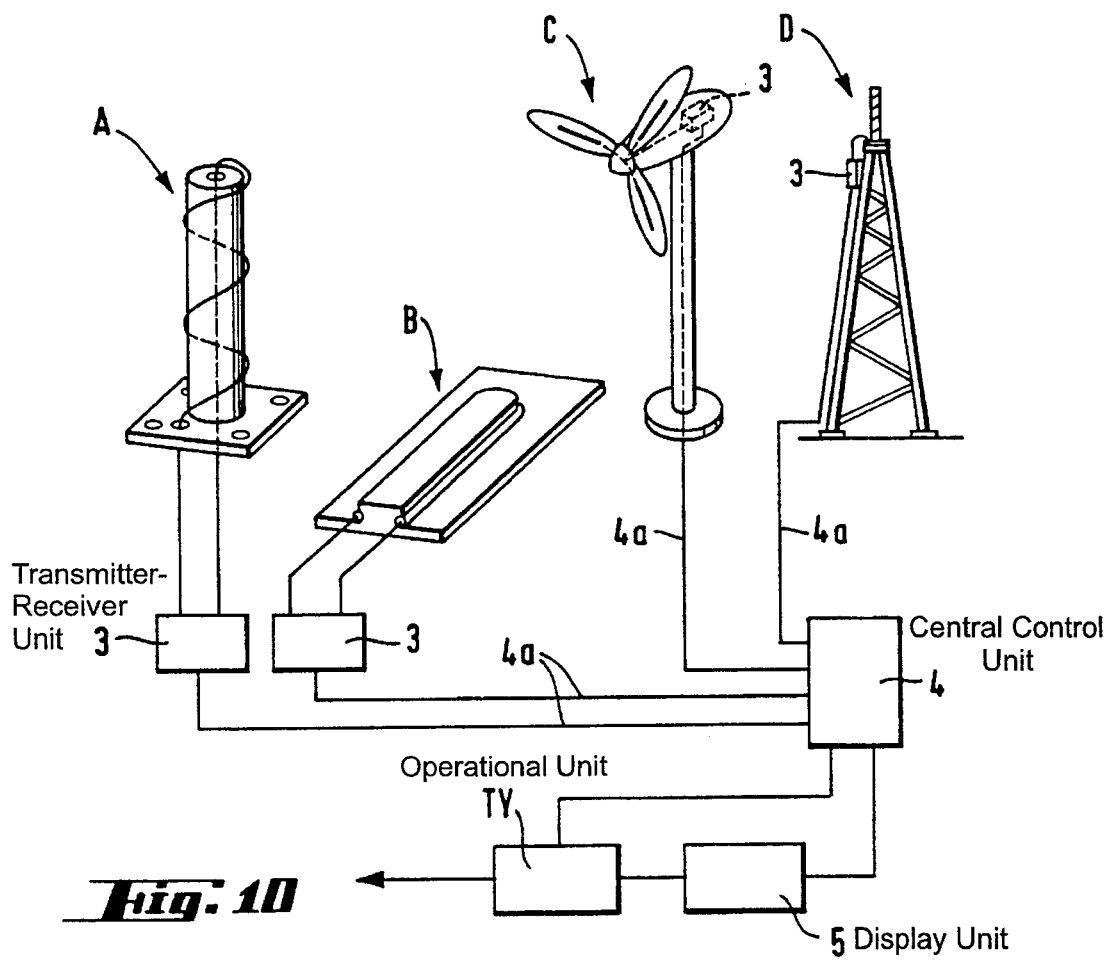
Figure 11:
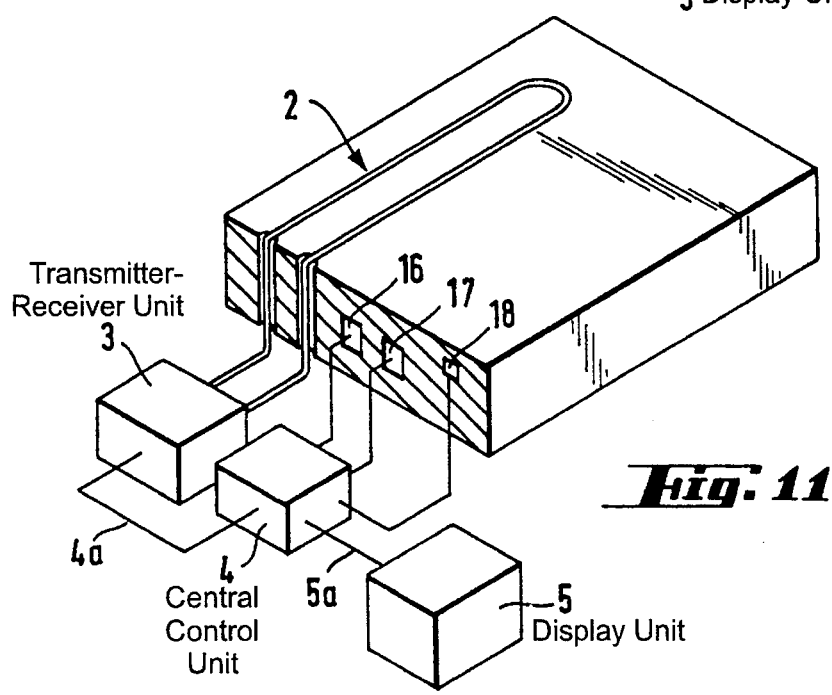

3a shows a cross-sectional view of said embodiment on a larger scale,

FIG. 4 is a schematic perspective view of a third embodiment of the sensor arrangement of the invention, FIG. 5 is a schematic perspective view of a fourth embodiment of the sensor arrangement of the invention, FIG. 6 is a schematic perspective view of a fifth embodiment of the sensor arrangement of the invention, FIG. 7 is a cross-sectional view of an embodiment of the lead-in arrangement, FIG. 8 is a schematic perspective view of part of an alternative application with reference to the second embodiment shown in FIG. 3, FIG. 9 shows the use of a combination of several embodiments of the sensor arrangement in connection with a ship, FIG. 10 shows the use of a combination of some sensor arrangements according to above-metioned embodiments, and FIG. 11 shows schematically an embodiment of the sensor arrangement for measuring road surface conditions.

DETAILED DESCRIPTION OF THE PREFERRED EMBODIMENT

Figure 1:
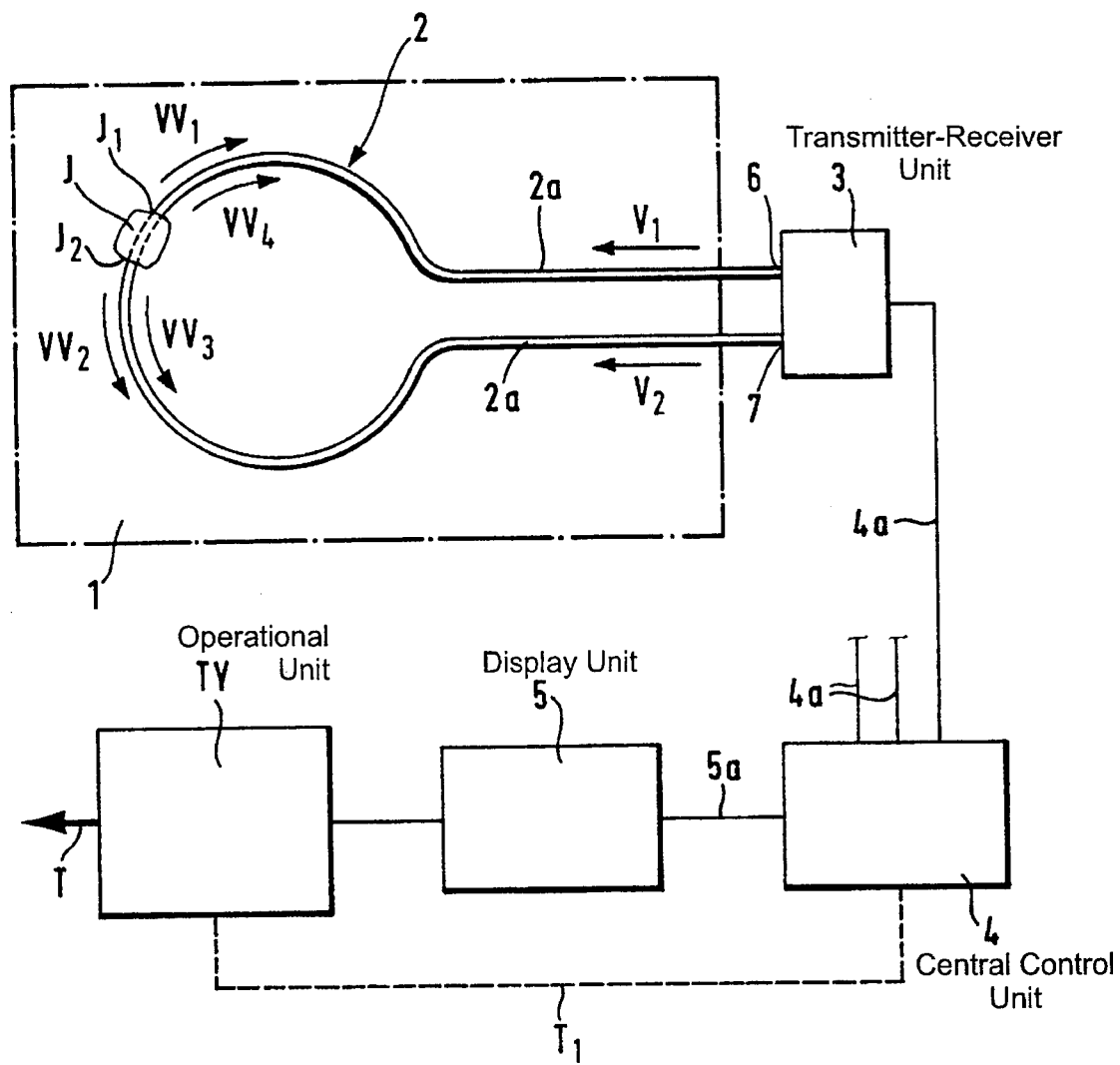
FIG. 1 is a schematic general view of a total system using the sensor arrangement.

FIG. 1 shows a general view of a total system in which one or several sensor arrangements of the invention can be applied for identifying different states of water. In FIG. 1, reference number 1 denotes a structure, a surface structure or a support structure, where the thread-like or band-like sensor element 2 of the sensor arrangement is placed upon the same. When water or different states of water are present on the surface of the structure 1, the sensor arrangement can be used for identifying the state of water in question.

The capability of the sensor arrangement to distinguish between the different states of water will remain even though chemicals of various types, such as glycol, salt, etc. were added into the water. The sensor element 2 is connected with the transmitter-receiver unit 3. As shown in FIG. 1, the sensor element 2 is arranged to form a loop with the transmitter-receiver unit 3, and both ends 6, 7 of the sensor element 2 are fixed thereto. In most embodiments, the loop-like sensor element 2 is, to secure many uses, advantageously placed in a functional manner in the frame 1. The loop is at least a part of the length of the sensor element 2 having also a parallel part 2a, in which the sections of the sensor element 2 are substantially aligned and at a distance from each other. Freezing will "close" the loop of the sensor element by combining the zones at a point $J_1$, for example, in FIG. 1.

The transmitter-receiver unit 3 operates as a local control unit which is electrically (line 4a) connected with a central control unit 4, which is, in turn, electrically connected (line 5a) with a monitor device, such as a display unit 5. For example on the basis of visual information from the display unit 5, the structure 1 can be subjected to such operations as melting or de-icing either by liquid spraying (glycol, salt, etc) or by electric heating. The operations T can be either carried out manually or automated to be part of the total system controlled by the central control unit (line $T_1$ to the operational unit TY).

In case of local ice formation at the point J of the sensor element 2, the sensor arrangement of the invention operates in the following manner. The transmitter-receiver unit 3 transmits oscillation in pulse form or pulse burst form in a first direction (e.g. counterclockwise) through the sensor element. The direction of transmission is shown by arrow $V_1$ in FIG. 1. Thus the transmitter-receiver unit 3 receives the response of the oscillation $V_1$ at the first end 6 of the sensor element 2 (transmitting end of the oscillation $V_1$). This response $VV_1$ is reflected from the first front edge of the ice formation J. On the other hand, the oscillation $V_1$ transmitted from the first end 6 is also reflected in the structure 1 (or in the support, cf. FIGS. 3 and 7), whereby it, having passed the ice formation J, is partially transmitted back to the sensor element 2. The second response $VV_2$ is thereby received at the second end 7 of the sensor element. A corresponding operation is carried out also by transmitting the oscillation from the second end of the sensor element as an oscillation $V_2$, whereby the responses of the oscillation $V_2$ are received in a corresponding manner as shown by arrows $VV_3$ and $VV_4$, whereby the second edge of the ice formation can be determined. The above-mentioned measuring signals are transmitted by the transmitter-receiver unit 3 to the central control unit 4 provided with a calculation program for detecting and locating the ice formation J in the range of the sensor element 2 numerically. The ice formation J can thus be located very precisely within the range on the basis of the position information received on its edges. Information on the ice formation J is received at the display unit 5, and possibly either manual or automatic measures T are taken after detecting the ice formation.

Consequently, the above-described embodiment is based on the following steps:

A) acoustic oscillation $V_1$ is transmitted to the sensor element 2 by the transmitter-receiver unit 3 at the first end 6 of the sensor element 2 whereby;

B) the first response $VV_1$ of the acoustic oscillation $V_1$ transmitted at the first end 6 and possibly reflected back from the measuring range of the sensor element 2 is received by the transmitter-receiver unit 3 at the first end 6 of the sensor element 2, the first response indicating a change in the state of water;

C) the second response $VV_2$ of the acoustic oscillation $V_1$ transmitted by the first end is received at the second end 7 of the sensor element 2 of the transmitter-receiver unit 3;

D) the steps A to C are carried out so that acoustic oscillation $V_2$ is transmitted by the second end 7 of the sensor element 2, whereby the responses $VV_3$, $VV_4$ of the acoustic oscillation $V_2$ transmitted to the sensor element 2 are received according to steps B and C;

E) the steps A to C are repeated at certain intervals by alternating the transmitting end 6, 7 of the acoustic oscillation $V_1$, $V_2$, if necessary, and;

F) the information from the transmitted oscillations $V_1$, $V_2$ and their responses $VV_1$, $VV_2$, $VV_3$, $VV_4$ is used for calculating the state of water in the measuring range of the sensor element 2.

Figure 2:
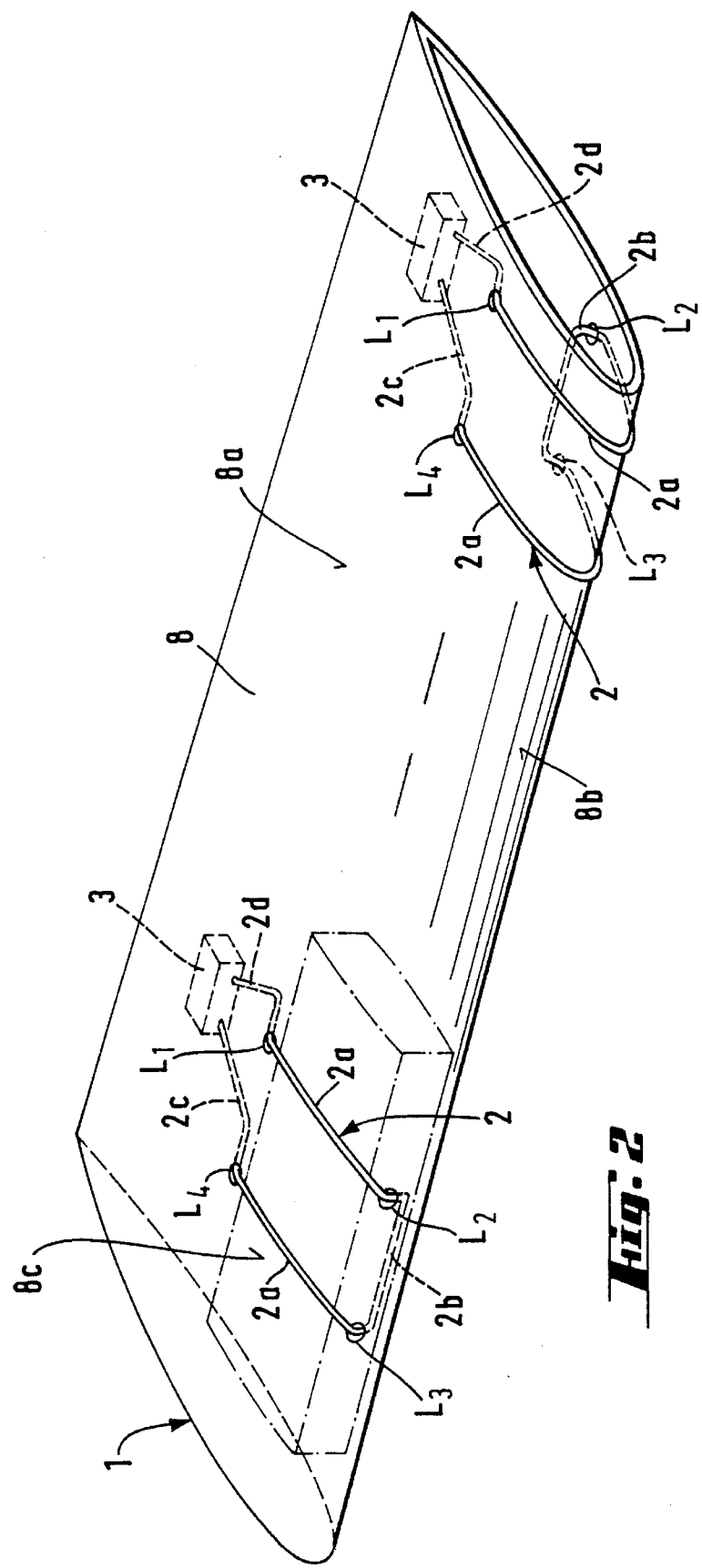
FIG. 2 shows two alternatives of the first embodiment of the sensor arrangement placed on the surface of a wing or a rotor.

FIG. 2 shows another embodiment of the sensor arrangement in two parts. The sensor arrangement is placed on a wing of an aircraft or on a rotor, e.g. a rotor of a wind power station, functioning as the structure 1. The left-hand part is intended to be placed on a surface 8a of a wing or rotor 8 subjected to icing. The right-hand part is intended for those purposes where the sensor arrangement measures the condition of the leading edge of the wing or rotor in addition to the surface 8a and thus overlaps the leading edge 8b. In both parts, the sensor element 2 has a loop form and is intended to be placed directly on the surface of the wing or rotor functioning as the structure 1. For achieving the loop form, the sensor element penetrates (lead-ins $L_1$, $L_2$, $L_3$, $L_4$) four times the surface of the structure 1. Each lead-in is provided with an insulating and clamping device, and the sensor element 2 is tightened against the outer surface of the wing or rotor, one embodiment of which is shown in FIG. 7. The sensor element 2 is thus placed on the first (outer) surface, and the transmitter-receiver unit 3 is placed on the side of the second surface of the structure 1, underneath the outer surface. The loop form of the sensor element 2 is achieved by connecting the suitably parallel measuring zones 2a of the sensor element 2 with each other by a clamp 2b of the material comprising the sensor element, as placed between the lead-ins $L_2$ and $L_3$ underneath the surface 8a. Attached to the lead-ins $L_1$ and $L_4$, the clamps 2c and 2d connect the sensor element to the transmitter-receiver unit 3.

In the case of an aircraft wing, it is advantageous to place the sensor element to overlap the interface boundary of the fuel tank. It is possible to monitor the condition on the surface 8a of both the fuel tank and a point where there is no fuel on the side opposite the surface 8a. The boundary of the fuel tank is designated by the numeral 8c in FIG. 2.

FIG. 3 shows an embodiment of the sensor arrangement where the sensor element 2, preferably pre-installed and tested, is placed on a support 9, through which the sensor element 2 is at least partly fixed on the first surface of the structure 1, such as a wing of an aircraft or a rotor. The support 9 is a longitudinal, flat form piece, its first bottom surface 10 being provided with fixing and support means 9a for fixing the sensor element 2 on the support 9. The fixing and support means 9a comprising the loop form of the sensor element 2 are arranged on the first surface of the support 9 in such a way that at least part of the length of the sensor element 2 forms a parallel part 2a where the sections of the sensor element are aligned, at a distance defined by the fixing and support means 9a of the support 9. The second bottom surface 11 is intended to be placed against the first (outer) surface of the structure 1. The lead-ins $L_1$ and $L_4$ and the clamps 2c and 2d can be arranged in a manner shown in FIG. 2. The support can fastened to the structure by screws 12 or by gluing, for example. The sensor arrangement shown in FIG. 3 can be used on the outer surface of a wing or rotor in a manner similar to the embodiments of FIG. 2. The support 9 is thus bent to correspond to the shape of the outer surface of the structure 1, i.e., to overlap the stagnation point.

The sensor element 2 and the support 9 form a strong structural entity which can be used to cover such sections of a wing where no screws can be fastened or which cannot be fixed in any another way. (The whole structure is mounted in a pre-installed form and tested against its support.)

In particular, FIG. 8 shows an alternative support, upon which the sensor element 2 is pre-installed to be ready for fixing to the structure 1. Thus the longitudinal form piece forming the support 9 is provided at its both longitudinal side surfaces with parts 13 protruding from the frame of the support 9. Further, the support 9 is formed of two pieces 9b, 9c to be fixed on top of each other. The protruding parts 13 are provided with grooves or the like in the longitudinal direction of the support 9 for receiving the sensor element 2. The protruding parts 13 are placed at a distance from each other in the longitudinal direction of the support 9, whereby free sections 13a, 13a' are formed in the longitudinal direction of the sensor element 2 at the side of the support between the protruding parts 13. The sensor element 2 is exposed to external conditions at the point. By changing the thickness of the lower support piece 9c it is possible to control the distance of the sensor element 2 from the structure 1. If needed, the protruding parts 13 can be provided with insulators for insulating the sensor element 2 from the support 9. In this embodiment, the protruding parts 13 and the grooves in them form the fixing and support means 9a for the sensor element 2. The support 9 is further provided with holes 12 for fastening screws.

FIGS. 4 and 5 show two additional embodiments of the sensor arrangement. FIG. 4 shows a support formed by a plate 14 or the like provided with fixing means 14a, such as holes, for fastening by screws, rivets or the like, and by a bar-like structure 15 protruding from the plate 14. The outer surface of the structure 15 is encircled by the first section 2' of the sensor element 2 penetrating the plate 14 or the like and extending to the upper end of the bar-like structure 15. The second section 2" is led through the inner hole 15c penetrating the bar-like structure 15 and parallel to its longitudinal direction, and connected to the transmitter-receiver unit 3. FIG. 5 shows an embodiment in which the bar-like structure 15 is U-shaped, whereby the ends 15a, 15b of the U-shaped structure 15 are provided with plates or the like 14' and 14" for fixing the sensor arrangement to the structure in a manner shown in FIG. 4. The sensor element 2 is wound around the U-shaped structure 15 the winding beginning with the clamp 2c extending from the transmitter-receiver unit 3. The sensor element penetrates through the plate 14' or the like, passes from the first end 15a to the second end 15b of the U-shaped structure 15, penetrates the plate 14' and is connected with the transmitter-receiver unit 3 by a clamp 2d.

FIG. 6 shows another embodiment of the sensor arrangement of the present invention. An element 15d forms a part of the actual bar-like structure 15 and is fastened to the rear part 15e by glueing or by screw fastening, particularly to form the leading edge of a wing. The element 15d comprises, in addition to the section 2e of the sensor element 2 on its surface, a heating resistance arrangement 16 intended for ice melting for example, two heating resistances in the longitudinal direction of the sensor element 2). This embodiment is provided with a plate 14 or the like shown in FIGS. 4 and 5 and with corresponding fastening means 14a forming part of the support. Consequently, the support comprises, like the element 15d, a rear part 15e protruding from the plate 14. The parts 15d and 15e form together the bar-like structure 15 which has the form of a wing profile when seen in a cross-section perpendicular to its longitudinal direction. The section 2e of the sensor element 2 is arranged against the stagnation point of the wing profile and aligned with it on the outer surface of the bar-like structure 15. The sensor element 2 is led to its section 2e via the inside of the bar-like structure 15 (section 2f). This section 2f of the sensor element 2 is connected at its ends to the transmitter-receiver unit 3. The heating resistance arrangement 16 in the front part of the wing profile is controlled by the central unit in a manner shown in FIG. 11.

The embodiment of FIG. 6 is particularly intended for use in connection with an aircraft and to be placed in the frame of the aircraft for monitoring possible formation of ice during the flight. The solution corresponding to the embodiment of FIG. 6 can also be applied by the structure of FIG. 2, whereby the sensor element 2 is led in alignment with the stagnation point of the wing or the rotor on at least part of the length of the wing or rotor.

FIG. 7 shows one embodiment for applying the lead-in arrangement shown with the general indexes $L_1$–$L_4$ in the previous figures. The structure 1 is provided with a hole R, through which the sensor element 2 is led from the side of the first surface to the side of the second surface of the structure 1. The hole has an insulation structure E for preventing leaks through the hole R. On the side of the second surface, there is a clamping device KR which is fastened to the structure 1 and comprises a support plate TL protruding diagonally from the second surface substantially at the hole R and provided with a longitudinal slot PR. The sensor element is fastened with a slide clamp LR which is arranged to be movable in the longitudinal direction of the slot PR and locked against the support plate TL with a locking screw L. The slide clamp LR is attached to the sensor element with a fastener K. The sensor element 2 can thus be tightened by transferring the slide clamp LR in the longitudinal direction of the slot PR onto the first surface of the structure 1, the clamps 2b-2d being free from the clamping effect.

In general, the clamping device thus comprises a first part (the support plate TL) and a second part (the slide clamp LR), of which the first one is fastened onto the second, or inner, surface of the structure 1 and the second one is fastened to the sensor element 2. The first and second parts are arranged to be movable in relation to each other for clamping the sensor element 2. The parts are locked in relation to each other by a locking device (for example, a locking screw). This construction can be modified in its structure to a great extent.

FIG. 9 shows an application of the total system in connection with a ship. Thus three sensor arrangements are placed on the mast M of the ship, in connection with the radar TU and the funnel S, for monitoring the condition at points important for the functions of the ship in a manner shown in FIG. 1.

FIG. 10 shows an embodiment of the invention, in which different embodiments of the sensor arrangement of the invention are used for multiple measurements of different states of water at several different locations. In the total system, a sensor arrangement A (FIG. 4) is used for monitoring the freezing of supercooled water. A sensor arrangement B is used for monitoring the situation at ground level such as a road surface (an embodiment of FIG. 3). Sensor arrangements C and D in connection with a rotor of a wind power station and/or in connection with a mast construction are used for monitoring the freezing of a fog cloud. The sensor arrangements according to the embodiment C can be constructed as shown in FIGS. 2 and 3, for example, and the sensor arrangements of the embodiment D can be similar to those shown in FIGS. 4 and/or 5. All these sensor arrangements are connected with the central unit 4 for carrying out further measures by means of the display 5 and the operational unit TY.

Further, FIG. 11 shows another embodiment of the sensor arrangement of the present invention. The sensor arrangement functions as part of the total measuring system in such a way that the sensor arrangement, at least the sensor element 2, is placed in the form piece funtioning as the support provided with e.g. electrically operated heating and cooling units 16 and 17 as well as one temperature-measuring sensor embedded therein. These parts are connected, in addition to the transmitter-receiver unit 3 of the sensor element 2, to the central unit 4 for monitoring the states and temperature of water under road conditions, on the surface of a main road, for example, and connected with a display 5 for informing automobile drivers, for example.

As shown in the above examples, it is possible to install the sensor arrangement in different structures by selecting a suitable embodiment for each structure in a manner that the sensor arrangement does not disturb the operation of the structure. Some examples of structures in which the sensor arrangement of the present invention can be applied are as follows: Aircraft wings, stabilizers, engine air inlets, helicopter rotors, rotors of wind power stations, ship structures, masts, davits and corresponding systems, radar and other antennas and mast structures, other vehicles and passages of the same. By combining different embodiments of sensor arrangements, it is possible to measure several different conditions of the environment simultaneously. The arrangements can be connected with one and the same central unit, as shown particularly in FIGS. 9 to 11. Thus the central unit can be used to control the required operations, such as visual information and/or melting measures etc. The total system can also be utilized by programming the central unit with logistics providing information for drawing various conclusions or deleting irrelevant information.

Particularly the embodiments of the sensor arrangement with the sensor element placed on a support (FIGS. 3 to 6 and 8) are intended for uses where the sensor element is subjected to various mechanical stresses, in connection with deicing on the wing of an aircraft or removal of ice upon heating the structure, the rotor of a wing power station, when the ice to be removed generates forces tending to detach the sensor element. It is obvious that the construction and choice of material of the support can also be used to control the movement of the signal from the sensor element to the support and/or to the structure in connection with the support and back to the sensor element for determination of the front and back edges of the local change of state.

As described above particularly in connection with the embodiment of FIGS. 6 and 11, the structure 1 and/or the support can also be provided with a heating and/or cooling unit for heating the structure 1 and/or the support and for melting the ice in connection with the structure 1 and/or the support. In case freezing is still going on after heating, by repeating the melting process at necessary intervals it will be detected that the state of water is found as ice under the measuring conditions and that the situation is still going on. The melting element can also be placed in the support in connection with the frame of the support 9, immediately against the head parts of the protruding parts 13 in the longitudinal direction of the support, as shown in the structure of FIG. 8.

Particularly in the embodiment of FIG. 11, it is advantageous that the support is formed as a piece simulating the conditions of a road with an asphalt coating and being placed away from the actual traffic road for preventing damage to the sensor system and the support.

The sensor arrangement can also be used for measuring other physical quantities, such as the temperature of the sensor element. The measurements of this kind can be made for purposes of the functioning of the total system, for example, for monitoring the working order of the sensor element. With particular reference to the embodiment of FIG. 2, the sensor element can be installed directly in various structures, such as aircraft wings, by lead-in arrangements not dampening ultrasound, whereby the sensor element can be transferred to extend inside the structure, on the side of the inner surface, for example. Thus a measuring range consisting of several measuring range parts is obtained by using a common sensor element for all measuring range parts. The lead-in part can comprise an insulating part, by means of which the sensor can be clamped on the surface of the structure 1 (cf. FIG. 2). The clamped sensor element is thus pressed tightly against the surface and it endures mechanical stresses, such as deicing, wind, etc. The sensor element according to the invention can also be formed of several elements, as is usually needed particularly for the clamp 2b in the embodiment of FIG. 2. The sensor wire can also be extended by a separate extension piece. This will facilitate the installation of the sensor wire or its repair upon break.

With reference to the above, the sensor arrangement according to the present invention has various applications as to its installation and use. The sensor arrangement can be applied either when fully mounted in place, or the sensor arrangement can be pre-installed on a support and tested under production conditions. In addition to the measuring results of the sensor arrangement, the total system can be used to combine several physical occurrences and information related to the change of state, including time, temperature, false alarm, operations by the user, etc.

We claim:

1. A method of identifying various states of water on a surface of a structure, comprising the steps of:

placing on said surface a sensor element having two ends and being made of an acoustically conductive material;

connecting a transmitter-receiver unit between said two ends of said sensor element;

alternately transmitting acoustic signals to each of said two ends; and receiving the corresponding acoustic signals from each of said two ends for processing thereof.

2. The method according to claim 1, wherein said step of signal processing includes determining a location of water in various states based on different amplitudes of said received signals returned from opposite edges of water in various states.

3. The method according to claim 1, further comprising the step of connecting a central control unit to said transmitter-receiver unit for determining a state of water based on numerical amplitudes of said transmitted and received signals.

4. A method of identifying various states of water on a surface of a structure, comprising the steps of:

(a) placing on said surface a sensor element having two ends and being made of an acoustically conductive material;

(b) connecting a transmitter-receiver unit between said two ends of said sensor element;

(c) transmitting an acoustic signal from said transmitter-receiver unit to a first end of said two ends;

(d) receiving a first acoustic signal from said first end, said first received acoustic signal corresponding to said transmitted acoustic signal being reflected from water in various states;

(e) receiving a second acoustic signal from a second end of said two ends, said second received acoustic signal corresponding to said transmitted acoustic signal passing through water in various states;

(f) repeating the steps (c) through (e) to said second end of said sensor element; and (g) repeating the steps (c) through (f) after a predetermined interval to determine a state of water based on amplitude of said received acoustic signals.

5. The method according to claim 4, further comprising the steps of connecting a central control unit to said transmitter-receiver unit and calculating said state of water based on numerical amplitudes of said transmitted and received signals.

6. The method according to claim 5, wherein said calculating step includes scaling said numerical amplitudes to the following ranges: (a) about 1.0–0.6 to indicate water, (b) about 0.6–0.2 to indicate slush, and (c) about 0.2–0.0 to indicate ice.

7. The method according to claim 4, further comprising the steps of connecting a central control unit to said transmitter-receiver unit and controlling the steps (c) through (g) via said central control unit.

8. A sensor arrangement for identifying various states of water on a surface of a structure, comprising:

a sensor element having two ends and being made of an acoustically conductive material, said sensor element adapted to be placed on said surface; and a transmitter-receiver unit connected between said two ends of said sensor element for alternately transmitting acoustic signals to each of said two ends and for receiving the corresponding acoustic signals from each of said two ends for processing thereof.

9. The sensor arrangement according to claim 8, wherein said sensor element forms a loop with said transmitter-receiver unit.

10. The sensor arrangement according to claim 8, wherein said sensor element is located on a first side of said structure, and said transmitter-receiver unit is located on a second side of said structure, and further comprising a lead-in arrangement which penetrates said structure to connect said sensor element with said transmitter-receiver unit.

11. The sensor arrangement according to claim 10, wherein said lead-in arrangement comprises clamping means which include a first part fixable to said structure and a second part fixable to said sensor element, and locking means which lock at a predetermined position said first and second parts which are moveable with respect to each other.

12. The sensor arrangement according to claim 8, further comprising a support attached to said structure, wherein said sensor element is partially placed on said support.

13. The sensor arrangement according to claim 12, wherein said support has a longitudinal flat shape and includes means for attaching said sensor element thereto.

14. The sensor arrangement according to claim 12, wherein said support is shaped substantially along a contour of said structure.

15. The sensor arrangement according to claim 12, wherein said support includes a plurality of protruding parts, and wherein said sensor element is spaced between two adjacent protruding parts of said plurality of protruding parts being exposed to external environmental conditions.

16. The sensor arrangement according to claim 12, wherein said support comprises means for changing physical conditions of various states of water.

17. The sensor arrangement according to claim 16, wherein said means include at least one of heating and cooling units.

18. The sensor arrangement according to claim 12, wherein said support comprises means for measuring environmental conditions.

19. The sensor arrangement according to claim 18, wherein said measuring means include a temperature sensor.

20. The sensor arrangement according to claim 8, wherein said two ends of said sensor element are spaced apart and substantially parallel with each other.

21. The sensor arrangement according to claim 8, further comprising a support having a tube-like shape and being attached to said structure for supporting said sensor element.

22. The sensor arrangement according to claim 21, wherein said support comprises at least one plate and means for attaching said support to said structure.

23. The sensor arrangement according to claim 21, wherein said support includes an opening therein, and wherein said sensor element is wound onto said support and passed through said opening for connecting with said transmitter-receiver unit.

24. The sensor arrangement according to claim 8, further comprising a U-shaped support being attached to said structure for supporting said sensor element, wherein said sensor element is wound substantially along a full length of said support.

* * * * *